(12) United States Patent
Bukhtiyarov et al.

(10) Patent No.: US 8,293,188 B2
(45) Date of Patent: Oct. 23, 2012

(54) DETECTION OF ADULTERATED SAMPLES

(75) Inventors: Yuri Bukhtiyarov, Boothwyn, PA (US); Cathey M Briggs, Landenberg, PA (US); Laura J Duggan, Newark, DE (US)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 0 days.

(21) Appl. No.: 12/711,970

(22) Filed: Feb. 24, 2010

(65) Prior Publication Data

US 2010/0150778 A1 Jun. 17, 2010

Related U.S. Application Data

(62) Division of application No. 11/159,944, filed on Jun. 23, 2005, now Pat. No. 7,695,975.

(51) Int. Cl.
*G01N 33/00* (2006.01)

(52) U.S. Cl. ....... 422/402; 422/68.1; 422/69; 422/82.05

(58) Field of Classification Search ................... 422/402, 422/68.1, 69, 82.05
See application file for complete search history.

(56) References Cited

U.S. PATENT DOCUMENTS

| | | | |
|---|---|---|---|
| 3,880,590 A * | 4/1975 | Ogawa et al. ................. | 422/420 |
| 4,440,724 A * | 4/1984 | Tabb et al. .................... | 422/420 |
| 4,789,638 A | 12/1988 | Kramer et al. | |
| 5,459,040 A * | 10/1995 | Hammock et al. ............ | 435/7.1 |
| 5,955,370 A | 9/1999 | Kell | |
| 6,503,726 B2 | 1/2003 | Anne et al. | |
| 6,689,618 B1 | 2/2004 | Chen | |
| 2002/0132267 A1 | 9/2002 | Wong | |
| 2002/0160439 A1 | 10/2002 | Anne et al. | |
| 2003/0045003 A1 | 3/2003 | Smith | |
| 2003/0138959 A1 | 7/2003 | Carter et al. | |
| 2003/0186451 A1 | 10/2003 | Smith | |
| 2004/0018636 A1 | 1/2004 | Zhou et al. | |
| 2004/0197235 A1 | 10/2004 | Sorensen | |
| 2004/0259186 A1 | 12/2004 | Paul | |

OTHER PUBLICATIONS

Hsu S M et al.: "Color modification of diaminobenzidine (DAB) precipitation by metallic ions and its application for double immunohistochemistry.", The Journal of Histochemistry and Cytochemistry: Official Journal of the Histochemistry Society Oct. 1982 vol. 30, No. 10, pp. 1079-1082.

Rye D B et al: "Stabilization of the tetramethylbenzidine (TMB) reaction product: application for retrograde and aterograde tracing, and combination with immunohitochemistry.", The Journal of Histochemistry and Cytochemistry: Official Journal of the Hitochemistry Society Nov. 1984 vol. 32, No. 11, pp. 1145-1153.

(Continued)

*Primary Examiner* — Sam P Siefke
(74) *Attorney, Agent, or Firm* — Theodore J. Leitereg

(57) ABSTRACT

In some embodiments, the present invention pertains to a method for detecting an adulterant in a biological sample. A combination of a biological sample, an agent for detecting the adulterant and an ionic moiety capable of undergoing reduction by gaining electrons is provided in an assay medium. The combination is incubated under conditions sufficient for the ionic moiety to undergo reduction and for the agent for detecting the adulterant to interact with the adulterant. The reduction of the ionic moiety enhances the detection of the adulterant as a result of increasing the sensitivity of the agent for detecting the adulterant. The extent of interaction between the agent for detecting the adulterant and the adulterant is measured and is related to the presence or absence of the adulterant in the biological sample.

3 Claims, 1 Drawing Sheet

OTHER PUBLICATIONS

Adams J C: "Heavy metal intensification of DAB-based HRP reaction product.", The Journal of Histochemistry and Cytochemistry: Official Journal of the Histochemistry Society Jun. 1981 vol. 29, No. 6, p. 775.

* cited by examiner

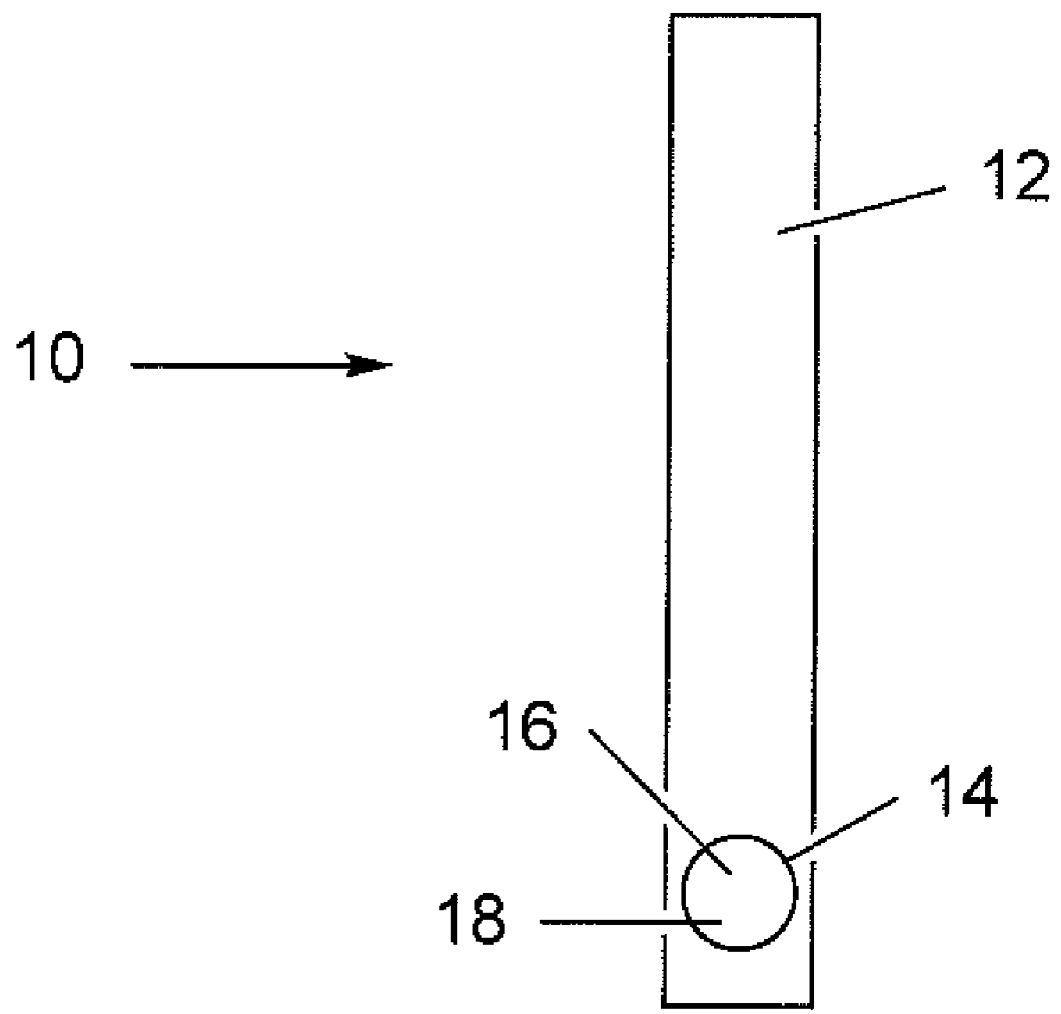

DETECTION OF ADULTERATED SAMPLES

This application is a divisional of U.S. Ser. No. 11/159,944, filed Jun. 23, 2005, now U.S. Pat. No. 7,695,975.

BACKGROUND

This invention relates to the determination of drugs of abuse. In some embodiments the invention relates to enhancing detection of adulterants that may be present in a biological sample to be tested for drugs of abuse.

As the use of illicit drugs has increased, public concern over the problems associated with its effects has grown. Drug use is generally recognized as a significant contributory factor in the current rise of accidents. Employers, government organizations, and others are increasingly using drug screening and freedom from drugs as conditions of employment. This concern has led to workplace drug testing in order to identify, treat, and remove active drug users from the workforce. Initial drug testing in the workplace revealed the obtrusive incursion of drug use and abuse in the daily lives of a significant portion of Americans. Further research indicated the staggering costs to public and private industry in terms of lost productivity, increased health care costs, and human suffering and death due to drug abuse. As a result, drug testing has spread to all areas of the public and private sector.

Because of the above, individuals may be requested or required to provide a sample such as a urine sample that will be tested for the presence of drugs of abuse or metabolites of drugs of abuse. An initial or screening test is frequently performed first. A positive result is usually confirmed by a method different from that used for initial testing, which usually has greater sensitivity and specificity than the initial test. An initial negative test, however, is usually not confirmed. Thus, an individual who is fearful of a positive result in an initial screening test may alter his or her urine sample to prevent detection of the drug or drug metabolite.

Many screening tests utilize antibody-antigen reactions quantified by means of an enzyme indicator. The confirmation assays, on the other hand, are labor and time intensive, highly accurate, expensive, and more difficult to adulterate. In addition, the positive screen has already raised a red flag, thereby drawing attention to the sample. The confirmation analysis utilizes GC-MS (gas chromatography mass spectrometry) testing which is considered the "gold standard" for drug assays scientifically and legally.

One method of altering a urine sample is by diluting the sample so that the drug or drug metabolite concentration is below the detection threshold in a screening test. For example, water and/or saline may be added to the sample to dilute the drug or its metabolite to a concentration that is less readily detected by the screening test. To detect this type of alteration, the urine sample is frequently assayed to determine if physiological parameters such as creatinine concentration, pH, and specific gravity are within normal ranges, or if these parameters are abnormal due to the presence of diluent.

Chemical adulterants may be added to a sample in an attempt to produce a false negative result in the initial screening test. In some instances, the chemical adulterants chemically convert a drug or a drug metabolite to a less detectable or non-detectable product. Adulteration techniques can be divided into two distinct types. The first utilizes an "in vivo" technique in which the user consumes the adulterant. The second technique utilizes an "in vitro" method in which the abuser adds the adulterant directly to the urine specimen submitted for testing.

In vitro methods utilize numerous products and compounds that will adversely affect either the screening or confirmation process. Products affecting the screening process include many household products and also commercially available products sold for the purpose of obscuring the result of a drug test. These products include oxidants such as, for example, hydrogen peroxide, sodium nitrite, bromates such as, e.g., sodium bromate, potassium bromate, etc., bromine, bleach (sodium hypochlorite), chromates such as, e.g., pyridinium chlorochromate, etc., nitrites, iodine, iodate, iodic acid, periodate, and the like.

The presence of chemical adulterants is more difficult to assess, since tests for the specific chemicals must be performed. As each new chemical adulterant is recognized and identified, tests are developed for identification of the specific adulterant. However, with the development of multiple adulterants, each of which is chemically distinct and each of which is capable of destroying or masking drugs of abuse or their metabolites, the process of identifying adulterated urine samples becomes increasingly difficult. Multiple tests must be performed on each sample to assure detection of all chemically adulterated samples. Furthermore, there is a period of time for each adulterant during which samples containing that adulterant are not detected because the test-specific adulterant has not yet been identified and/or confirmed.

Sample adulteration can affect many of the commonly used methods for to detection of drugs of abuse including, for example, enzyme immunoassay (EMIT or EIA), radioimmunoassay (RIA), and florescent polarization immunoassay (FPIA) and so forth. Consequently, clinical chemistry literature recommends, and SAMSHA Mandatory Guidelines for Federal Workplace Drug Testing Programs now require, that testing for drugs of abuse in urine samples include testing for adulterants to identify urine samples that have been adulterated.

Various compositions and methods have been developed to detect one or more of a group of adulterants that are added to biological samples such as urine to prevent detection of drugs of abuse. Examples of such compositions include chromophoric agents such as, for example, 3,3',5,5'-tetramethylbenzidine, diaminobenzidine, 3-amino-9-ethylcarbazone, 4-chloro-1-napthol, 2,2-azino-bis(3-ethylbenzthiazoline-6-sulfonic acid, ortho-phenylene-diamine, and so forth.

There is a need for enhancing detection of adulterants in samples for analysis of drugs of abuse. In particular, there is a need for increasing sensitivity of compositions used for detection of adulterants. The enhanced detection of adulterants should be realized for both manual and automatic processes.

SUMMARY OF EMBODIMENTS OF THE INVENTION

In some embodiments, the present methods are employed for detecting an adulterant in a biological sample. A combination of a biological sample, an agent for detecting the adulterant and an ionic moiety capable of undergoing reduction by gaining electrons is provided in an assay medium. The combination is incubated under conditions sufficient for the ionic moiety to undergo reduction and for the agent for detecting the adulterant to interact with the adulterant. The reduction of the ionic moiety enhances the detection of the adulterant as a result of increasing the sensitivity of the agent for detecting the adulterant. The extent of interaction between the agent for detecting the adulterant and the adulterant is measured. The extent of the interaction is related to the presence or absence of the adulterant in the biological sample.

In some embodiments of the methods for detecting an oxidant adulterant in a biological sample, a combination of a biological sample, a chromogenic compound and a source of ferric ions is provided in an assay medium. The combination is incubated under conditions sufficient for the ferric ions to undergo reduction to ferrous ions and for the chromogenic compound to interact with the oxidant adulterant. The extent of interaction between the chromogenic compound and the oxidant adulterant is determined and the extent thereof is related to the presence or absence of the oxidant adulterant in the biological sample.

Some embodiments of the present invention are directed to a test device comprising a support that comprises one of both of an agent for detecting an adulterant in a biological sample and a source of metal ions.

In some embodiments the present invention is directed to kits comprising in packaged combination an agent for detecting an adulterant in a biological sample and a source of metal ions.

BRIEF DESCRIPTION OF THE DRAWINGS

The following figures are included to better illustrate the embodiments of the apparatus and technique of the present invention. The figures are not to scale and some features may be exaggerated for the purpose of illustrating certain aspects or embodiments of the present invention.

FIG. 1 is a schematic depicting an embodiment of a device in accordance with embodiments of the present invention.

DESCRIPTION OF SPECIFIC EMBODIMENTS

Before the subject invention is described further, it is to be understood that the invention is not limited to the particular embodiments of the invention described below, as variations of the particular embodiments may be made and still fall within the scope of the appended claims. It is also to be understood that to the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

Embodiments of the present methods are employed in conjunction with the examination of biological samples for the presence of one or more drugs of abuse where there is an interest in determining whether the biological sample has been adulterated. An ionic moiety that is capable of undergoing reduction is used to increase the sensitivity of an agent for detecting the presence of an adulterant in the biological sample.

The terms "drugs of abuse" or "analyte" includes the drugs themselves and their metabolites and the like and may include therapeutic drugs that are otherwise legal but are misused. The drugs of abuse are generally from about 100 to about 2,000 molecular weight, or from about 125 to about 1,000 molecular weight. Representative drugs of abuse (including misused drugs), by way of example and not limitation, include (i) alkaloids such as morphine alkaloids, which include morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites; (ii) steroids, which include the estrogens, androgens, andreocortical steroids, bile acids, cardiotonic glycosides and aglycones, which includes digoxin and digoxigenin, saponins and sapogenins, their derivatives and metabolites; steroid mimetic substances, such as diethylstilbestrol; (iii) lactams having from 5 to 6 annular members, which include the barbiturates, e.g., Phenobarbital and secobarbital, diphenylhydantoin, primidone, ethosuximide, and their metabolites; (iv) aminoalkylbenzenes, with alkyl of from 2 to 3 carbon atoms, which include the amphetamines; catecholamines, which include ephedrine, L-dopa, epinephrine; narceine; papaverine; and metabolites of the above; (v) benzheterocyclics which include oxazepam, chlorpromazine, tegretol, their derivatives and metabolites, the heterocyclic rings being azepines, diazepines and phenothiazines; (vi) purines, which includes theophylline, caffeine, their metabolites and derivatives; (vii) drugs derived from marijuana, which include cannabinol and tetrahydrocannabinol; (viii) hormones such as thyroxine, cortisol, triiodothyronine, testosterone, estradiol, estrone, progesterone, (ix) tricyclic antidepressants, which include imipramine, dismethylimipramine, amitriptyline, nortriptyline, protriptyline, trimipramine, chlomipramine, doxepine, and desmethyldoxepin; and (x) anti-neoplastics, which include methotrexate; and the like.

The analyte may be a molecule found directly in a sample such as biological sample, which term includes body fluids or tissue from a host. The sample can be examined directly or may be pretreated to render the analyte more readily detectable by removing unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, such as methanol; and treatment with detergents. The sample can be prepared in any convenient medium, which does not interfere with an assay. An aqueous medium is preferred.

The phrase "biological sample" refers to any biological material such as, for example, body fluid, tissue and the like, which is obtained from the body of a mammal and which is suspected of containing one or more drugs of abuse. Body fluids include, for example, whole-blood, plasma, serum, interstitial fluid, sweat, saliva, urine, semen, blister fluid, inflammatory exudates, stool, sputum, cerebral spinal fluid, tears, mucus, lymphatic fluid, vaginal mucus, and the like. The biological tissue includes excised tissue from an organ or other body part of a host, e.g., tissue biopsies; hair and skin; and so forth.

The adulterants mentioned above include any substance (or combination thereof) that may be added to the biological sample to be tested either by direct addition or by indirect addition such as by ingestion and the like. The substance is added to the biological sample to adversely affect a screening assay or a confirmation process. Such substances include many household products and also commercially available products sold for the purpose of obscuring the result of a drug test. The substance may be an oxidation-based adulterant or oxidant such as, for example, a nitrite such as, e.g., sodium nitrite, etc., a bromate such as, e.g., sodium bromate, potassium bromate, etc., bromine, bleach (sodium hypochlorite), a chromate such as, e.g., pyridinium chlorochromate (chromium VI), etc., a peroxide, e.g., hydrogen peroxide, etc., either alone or in conjunction with a peroxidase enzyme, an iodine containing compound such as, for example, iodine, iodate, e.g., sodium iodate, etc., iodic acid, periodate, e.g., sodium periodate, etc., and the like. Many of the above substances are relatively strong oxidizing agents and are the active ingredient in many commercial products specifically sold for the purpose of adulterating biological samples.

Other adulterants to which the present methods may find application, other than a general oxidant test, include, for example, enhancement of a test for a specific oxidant such as, e.g., bleach or nitrite, and the like.

The amount of adulterant that may be in a biological sample is usually that which is added by an external source either directly or indirectly as discussed above. The amount of adulterant is dependent on the nature of the adulterant, the nature of the biological sample, the nature of the assay being used to detect the drug of abuse, and so forth. The amount of adulterant added is usually at least that which is sufficient to render an assay for a drug of abuse ineffective in detecting the drug of abuse and may be greater but not so great as to render the adulterant readily detectable by visual or other inspection. In general, the amount of adulterant in the biological sample can vary wildly depending on how much an individual adds to the sample; but, in general, such individual would only want to add enough adulterant to render the initial screen negative and not enough to change the physical appearance or odor of the sample. Obviously, the amount of adulterant in the assay medium is dependent on the amount in the biological sample, which may be diluted by additional components of the assay medium.

Various agents for detecting adulterants have been developed. Such agents include, for example, chromogenic compounds, and the like, which are most easily subject to automation. Detection may also occur by measurement of physical properties such as, for example, pH, specific gravity, and the like.

As mentioned above, one group of agents for detecting adulterants includes chromogenic compounds that are capable of being oxidized by the adulterant to produce a product detectable by visual or other inspection, usually, a colored product. The phrase "capable of being" means that the particular substance will undergo the recited operation if the conditions for the operation are present. For example, capable of being oxidized means that the substance will undergo oxidation to a detectable level when the adulterant is present. Examples of chromogenic compounds include, by way of illustration and not limitation, 2,2-azino-bis(3-ethylbenzthiazoline-6-sulfonic acid (ABTS); 3-amino-9-ethylcarbazone; naphthols such as, for example, 4-chloro-1-napthol, and the like; phenylamine chromogenic indicators such as, for example, N,N,N,N-tetramethyl-1,4-phenylenediamine, N,N-diethyl-1,4,-phenylenediamine, 2,3,5,6-tetramethyl-1,4-phenylenediamine, N,N-dimethyl-p-phenylenediamine, 2,4,6-trimethyl-1,3-phenylenediamine, N,N,N,N-tetramethylbenzidine, 3,3,5,5-tetramethylbenzidine, N,N,N,N-tetramethyl-4,4-diaminestilbene, diamine-benzidine, ortho-phenylene-diamine, and O-toluidine, and so forth. Particular examples of chromogenic compositions for detecting adulterants may be found in U.S. Pat. No. 6,503,726 (Anne, et al.), and U.S. Patent Publication No. 20030138959 (Carter, et al.), the disclosures of which are incorporated herein by reference.

The amount of agent for detecting an adulterant is that which is sufficient to render an assay for the adulterant effective in, or sufficient for, detecting the adulterant and is dependent on the nature of the agent, the nature of the adulterant, the nature of the biological sample, composition of the sample as a result of the health of the individual and any medications or vitamins they may ingest, and so forth. In general, the amount of agent for detecting an adulterant in the assay medium is variable depending on the redox potential of the agent itself. In many instances the amount of agent employed for detecting an adulterant is specified by the manufacturer of the product comprising the agent.

As mentioned above, in accordance with embodiments of the present invention, an ionic moiety capable of undergoing reduction by gaining electrons is included in a medium comprising the biological sample and the agent for detecting the adulterant. The nature of the ionic moiety is related to the nature of the agent for detecting the adulterant. The ionic moiety must not deleteriously affect to any significant extent the activity of the agent for detecting the adulterant. The ionic moiety is particularly effective in enhancing the sensitivity of agents for detecting oxidation-based adulterants. In some embodiments the ionic moiety is a metal ion of a metal such as, for example, a Group VIII metal, a Group VIIB metal, a Group IB metal, and the like. For example, metals include iron, silver, copper, manganese, nickel, platinum, and so forth. Examples of suitable metal ions include ferric, silver (+1), cupric, manganese (+4), nickel (+2 and +4)), platinum (+4), and the like. For example, ferric ion is capable of gaining electrons to go from the $Fe^{+3}$ state to the $Fe^{+2}$ state.

The metal ion is usually present with a co-ion, which should not affect to any significant extent the activity of the agent for detecting the adulterant. The co-ion should not itself be an adulterant. Examples of suitable co-ions include, for example, chloride, sulfate, bromide, fluoride, iodide, oxide, and the like. The ionic moiety and its co-ion may be present in the dry state or in solution, usually in an aqueous medium. If present in solution, the amount of the ionic moiety is sufficient such that, when the solution is added to an assay medium or becomes an assay medium, the ionic moiety is present in the desired amount or concentration in accordance with embodiments of the present invention.

The amount of ionic moiety is that which is sufficient to enhance the sensitivity of the agent for detecting the adulterant and is dependent on the nature of the agent, the nature of the adulterant, the nature of the biological sample, and so forth. The amount of the ionic moiety is usually determined on an empirical basis. In general, the amount of ionic moiety in the assay medium is small compared to the concentration of the chromogenic portion of the assay. As an example using ferric ion for purposes of illustration and not limitation, in many embodiments the concentration of the ferric ion in the resultant assay medium (i.e., after addition of ferric ion as a solid or liquid reagent) is about 0.1 to about 100 μg/mL, about 0.5 to about 50 μg/mL, about 1 to about 30 μg/mL, about 2 to about 10 μg/mL, and so forth.

In some embodiments the ionic moiety is provided as a separate reagent either in a suitable liquid medium or in the dry state. Various buffers may be employed to assist in maintaining a pH to enhance solubility of the ionic moiety in an aqueous medium, which may be similar to the aqueous media discussed above for the assay medium. The nature of the buffer will depend on the nature of the ionic moiety including its solubility requirements. Other materials may also be present with the ionic moiety such as stain preventing materials and the like. For example, sodium dodecyl sulfate may be employed at a concentration that reduces or eliminates staining of assay reaction vessels so that the vessels may be reused after suitable washing.

The examination of the biological sample for the presence of the adulterant is usually carried out in an assay medium, which may be a medium that is the same as, or different from, the medium for conducting an assay for the detection of the drug of abuse. In some embodiments the biological sample provides the assay medium, which is contacted with an assay medium comprising the agent for detecting an adulterant, an ionic moiety, buffers and the like are added. Various buffers may be added to the biological sample to adjust pH and the like. In some embodiments the assay medium is an aqueous buffered medium to which the biological sample and other agents are added. The pH of the assay medium is low to moderate, generally that which provides optimum assay sensitivity. The aqueous medium may be solely water or may include from 0.1 to about 40 volume percent of a cosolvent such as, for example, an organic solvent, e.g., an alcohol, an ether, and the like. The pH for the medium will usually be in the range of about 2 to about 11, about 4 to about 11, more usually in the range of about 5 to about 10, and preferably in the range of about 6.5 to about 9.5. The pH will usually be a compromise between that which is optimum for bringing about interaction between the agent for detecting the adulterant and the adulterant and the reduction of the ionic moiety, and so forth.

Various buffers may be used to achieve the desired pH and maintain the pH during the determination. Illustrative buffers include borate, phosphate, carbonate, tris, barbital and the like. The particular buffer employed is not critical to this invention, but in an individual assay one or another buffer may be preferred. Various ancillary materials may be employed in the above methods. For example, in addition to buffers the medium may comprise stabilizers for the medium and for the reagents employed. Frequently, in addition to these additives, proteins may be included, such as albumins; organic solvents such as formamide; quaternary ammonium salts; polyanions such as dextran sulfate; surfactants, particularly non-ionic surfactants; binding enhancers, e.g., polyalkylene glycols; or the like.

As mentioned above, a combination of the biological sample, which is suspected of containing an adulterant, an agent for detecting an adulterant, and the ionic moiety is formed in an assay medium. While the order of addition may be varied widely, there will be certain preferences depending on the nature of the assay. The simplest order of addition is to add all the materials simultaneously and examine the medium for the presence of a signal indicating the presence of the adulterant in the biological sample. Alternatively, the reagents can be combined sequentially. Optionally, an incubation step may be involved subsequent to each addition as discussed above.

The combination is incubated under conditions sufficient for the ionic moiety to undergo reduction and for the agent for detecting the adulterant to interact with the adulterant. One or more incubation periods may be applied to the medium at one or more intervals including any intervals between addition of various reagents mentioned above. The medium is usually incubated at a temperature and for a time sufficient for the various interactions to occur. Moderate temperatures are normally employed for carrying out the method and usually constant temperature, preferably, room temperature, during the period of the measurement. Incubation temperatures range from about 5° to about 99° C., from about 15° C. to about 70° C., from about 20° C. to about 45° C. The time period for the incubation is about 0.2 seconds to about 6 hours, about 2 seconds to about 1 hour, about 1 to about 5 minutes. The time period depends on the temperature of the medium the rate of the various interactions, and so forth. Temperatures during measurements will generally range from about 10 to about 50° C., from about 15 to about 40° C.

The nature of the signal that is observed is dependent on the nature of the agent for detecting an adulterant. For chromogenic compositions, the signal is usually a color that is detectable either visually or instrumentally or both. For example, clinical instruments that are employed currently to measure color formation in assays conducted in clinical laboratories may be employed. The level of the signal detected is related to the presence of the adulterant in the biological sample. In general, a predetermined cut-off level is established for the adulterant. The particular predetermined cut-off level generally is determined on an adulterant-by-adulterant basis. Those skilled in the art are well aware of the factors relating to the selection of predetermined cut-off levels. Usually, the predetermined cut-off level is dependent on the smallest amount of adulterant that is necessary to render the assay for a drug of abuse ineffective.

The format for conducting the determination of an adulterant in accordance with embodiments of the present methods is dependent on the nature of the adulterant, the nature of the agent for detecting the adulterant, the nature of the ionic moiety, the nature of the sample, and so forth. The assay may be carried out in a reaction vessel such as, for example, a well of a microtiter plate, a cuvette, test tube, an automated instrument which can process sample, and the like. In some embodiments the reagents may simply be added to the reaction vessel along with the biological sample and the medium is then examined for the presence and/or amount of a signal. In some embodiments one or more of the reagents may be present on a support such as, for example, a porous member, which may be contacted with the assay medium or on which the assay is carried out. One or more of the reagents may be attached to a support diffusively such as, for example, by impregnation, drying, adsorption, and the like, or non-diffusively such as, for example, by covalent binding and the like.

In some embodiments one or more of the reagents may be present on a porous member usually in a diffusive manner so that the reagents may dissolve in the assay medium. In some circumstances one or more of the reagents may be present on the porous member in a non-diffusive manner. The present embodiments have application to all assay formats for detecting adulterants in biological samples.

In some embodiments the porous member comprises a porous material having pores of at least 0.1 microns, at least 1.0 micron, may be employed. The porous material can be attached to a support. On the other hand, the porous material may provide its own support. The porous material may be functionalized to permit bonding of one or more reagents for performing embodiments of the present methods. On the other hand, the porous material may be of such composition that one or more reagents are bound in a non-covalent manner by adsorbtion, impregnation, and the like.

For example, in some embodiments impregnation is employed, which can be carried out in one or more impregnation steps. Each impregnation may contain one or more of the chemical compounds making up the assay reagent composition; the exact procedure is dictated by the inter-reactivity of the assay constituents and the order in which they may have to react with each other or the adulterant depending on the particular protocol and reagents employed. The impregnation may be carried out with solutions of the required reagents in volatile solvents, such as water, methanol, ethanol or acetone. This may be accomplished in one impregnating step. Frequently however, it is advisable to carry out the impregnation in several steps where multiple solutions are used, which in each case contain one or more of the reagents.

The porous materials are generally hydrophilic or are capable of being rendered hydrophilic and preferably are cellulosic materials and materials derived from cellulose, such as fiber containing papers, e.g., filter paper, chromatographic paper, etc., but may include inorganic powders such as silica, magnesium sulfate, and alumina; and other natural polymeric materials, and synthetic or modified naturally occurring polymers, such as nitrocellulose, cellulose acetate, poly(vinyl chloride), polyacrylamide, cross linked dextran, agarose, polyacrylate, etc.; either used by themselves or in conjunction with other materials; ceramic materials; and the like.

The piece of porous member can be a single structure such as a sheet cut into strips or pads or it can be several strips or pads or particulate material. The porous member can have a rectangular, circular, oval, triagonal or other shape. The porous member in a desired form may be bound to a support or solid surface such as found, for example, in thin-layer chromatography and may have an absorbent pad either as an integral part or in liquid contact. The porous member can be comprised of several segments in liquid receiving relationship and preferably bound to a support. The porous member can also be a sheet having lanes thereon or capable of spotting to induce lane formulation, wherein a separate assay can be conducted in each lane.

The support for one of more of the reagents above or for the porous member, where a support is desired or necessary, will normally be water insoluble, non-porous, and rigid and usually will be of the same length and width as the bibulous member but may be larger or smaller. A wide variety of organic and inorganic materials, both natural and synthetic, and combinations thereof, may be employed provided only that the support does not interfere with the function of the porous member or the reagents for the assay. Illustrative polymers include polyethylene, polypropylene, poly(4-methylbutene), polystyrene, polymethacrylate, poly(ethylene terephthalate), nylon, poly(vinyl butyrate), poly (vinyl chloride), polyacrylamide, polyacrylate, and the like, either used by themselves or in conjunction with other materials. Other support materials include, for example, glass, ceramics, metals, and the like. The support can have any one of a number of shapes, such as strip, rod, plate, well, particle, bead or the like.

The porous member may be partially or substantially completely enclosed in a protective casing, conveniently a clear or partially, or in some situations completely, opaque enclosure. Depending upon the particular protocols involved and the construction of the device, the enclosure may be removable or irremovable, may encase only the porous member or may encase additionally all or a portion of a support. The enclosure may provide for one or more windows and will normally be of a sturdy inert impermeable material that will provide mechanical protection for the porous member and will not interfere with the performance of the assay. Normally an air opening will be provided to prevent the entrapment of air within the enclosure.

In a strip format where an assay medium traverses at least a portion of the porous member, the porous member may have a length of about 1.5 to about 30 cm, about 2 to about 20 cm. The width may vary from about 0.1 mm to about 3 cm. The thickness will generally be about 0.1 mm to about 5 mm, from about 0.5 to about 3 mm. In a pad format, the porous member will generally have a thickness of about 0.5 to about 10 mm and an area of about 25 to about 150 square millimeters ($mm^2$).

Exemplary formats as are known in the art are discussed below by way of illustration and not limitation. In one format, the agent for detecting the adulterant is impregnated in a pad to provide a test strip immunoassay. In accordance with embodiments of the present invention, an ionic moiety is either also impregnated in the pad or added to an assay medium comprising the biological sample, which is contacted with the pad.

In another exemplary format, a device using assay strips is employed where two sets of parallel strips are mounted back-to-back. Each set of strips is visible through a window on the front or back faces of the device. The assay medium comprising the biological sample is contacted with the device through an aperture in the device enclosure and carried to the test strips by a wick in the form of a piece of blotting paper. Contact of the assay medium may be carried out by means of a pipette or the bottom portion of the device can be dipped in a container comprising the assay medium. One of the test strips visible through a separate window is used to detect an adulterant in the biological sample and, accordingly, comprises an agent for detecting the adulterant. An ionic moiety in accordance with embodiments of the present invention is present on the test strip or in the assay medium.

Other exemplary formats involve test strips in the form of dry chemistry dipsticks, or on-site test modules utilizing thin layer chromatography in a lateral flow format, or other similar technology. After impregnation, the dipsticks are dried, cut into strips, glued to a support as part of a "sandwich" composed of a handle, test pad. A portion of or the entire dipstick may be enclosed in a synthetic resin film and/or a fine-mesh material and/or water stable film as known in the art.

An embodiment of a test device is shown in FIG. 1. Test device 10 comprises porous pad 12 affixed to a plastic strip 14. Pad 12 is impregnated with an agent for detecting an adulterant 16 and with an ionic moiety 18.

Kits

Another aspect of the present invention relates to kits useful for conveniently performing an assay for the determination of an adulterant in a biological sample. In some embodiments the kits comprise in packaged combination an agent for detecting an adulterant in a biological sample and a source of metal ions. In some embodiments the kits comprise a test device 10 as described above and one or more buffers for addition to an assay medium. In some embodiments the kits comprise a test device comprising an agent for detecting an adulterant and separately packaged ionic moiety reagent as well as one or more buffers, one or more bulk reagents for an automated device, and so forth. In some embodiments the kits comprise a test device that comprises a strip, plate, well.

To enhance the versatility of the subject invention, the kit reagents can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents. Furthermore, one or more of the above reagents may be present on a porous member of a device. The kit can further include other separately packaged reagents for conducting an assay such as additional binding members, ancillary reagents such buffers, and to so forth. The relative amounts of the various reagents in the kits can be varied widely to provide for concentrations of the reagents that substantially optimize the reactions that need to occur during the present method and further to optimize substantially the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. The kit can further include a written description of a method in accordance with the present invention as described above.

Use of Embodiments

Embodiments of the present invention may be utilized in conjunction with many known assays for drugs of abuse. The assay methods usually involve a biological sample, which is combined in an assay medium with reagents for carrying out the assay. Such reagents may include a binding partner for the analyte such as, e.g., an antibody for the analyte, analyte analogs, solid surfaces to which one of the above reagents is bound, binding partners for binding partners, and so forth. One or more of the reagents can be labeled with a label such as, e.g., an enzyme. The reagents are chosen such that a signal is obtained from a label in relation to the presence or amount of analyte in the sample.

The assays can be performed either without separation (homogeneous) or with separation (heterogeneous) of any of the assay components or products. Homogeneous immunoassays are exemplified by the EMIT® assay (Dade Behring Inc.) disclosed in Rubenstein, et al., U.S. Pat. No. 3,817,837; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and so forth.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the is combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"), etc.; and the like.

Exemplary of heterogeneous assays are the enzyme linked immunosorbant assay ("ELISA") discussed in Maggio, E. T. supra; the radioimmunoassay, disclosed in Yalow, et al., *J. Clin. Invest.* 39:1157 (1960) and so forth.

Embodiments of the present invention may also be utilized in conjunction with multi-analyte immunoassays where one or more drugs of abuse. Such multi-analyte systems are described, for example, in Loor, et al., J. Anal. Toxicol. 12: 299 (1988).

As mentioned above, after an initial screening assay is performed, biological samples yielding positive results are subjected to a confirmation, assay, such as, for example, GC-MS to verify the results of a positive screen for drugs of abuse. The GC-MS analysis costs many times more than an initial screen. Every additional unnecessary GC-MS performed drives up the overall cost of drug testing. Eliminating these additional, unnecessary assays saves millions of dollars per year. As a result of conducting an assay for an adulterant in accordance with embodiments of the present invention, unnecessary time and reagents may be saved. Tests may be halted as soon as the presence of the adulterant is detected. The ability to terminate the screening process by ascertaining the presence of an adulterant results in reduced technician's efforts and time, providing an economic savings to the testing laboratory. Furthermore, the early interruption and cessation of the automated screening process may facilitate earlier recovery of a substitute biological sample from the person being tested, providing more accurate determinations to the requestor of the testing.

Furthermore, false positive drug screens strongly impact on-site testing. In most situations utilizing on-site tests (on site devices such as dipstick or lateral flow devices require no instrumentation, making these devices ideal for collection and on site facilities) the employee is screened upon arrival for work. If a positive is obtained using the on-site test, a second sample is forwarded to the lab for GC-MS confirmation and the employee is suspended from work or reassigned to other duties until the results of the test are known. Therefore, it is of vital importance that the employer and laboratory know if the sample has had an adulterant added to save time, money, and so forth.

The invention is demonstrated further by the following illustrative examples.

EXAMPLES

Parts and percentages herein are by weight unless otherwise indicated. Temperatures are in degrees Centigrade (° C.). All materials were from Sigma-Aldrich, Saint Louis Mo. unless indicated otherwise.

Materials: Reagent 1 (agent for detection of an adulterant) contained 0.42 g/L of 2,2'-Azino-bis(3-ethylbenzothiazoline-6-sulfonic acid) diammonium salt in 50 mM Glycine-HCl at pH 2.1 with 0.01% sodium dodecyl sulfate (SOS). Reagent 2 (in accordance with some embodiments of the invention) contained 12.2 µg/mL of ferric chloride in 50 mM Glycine-HCl at pH 2.1 with 0.01% SDS. 247 µL of Reagent 1 was mixed with 103 µL of Reagent 2 and 5 µL of sample, which was prepared at the appropriate test concentrations as set forth in the table below. The mixture was incubated at 37° C. for 13 minutes and the absorbance was measured at 700 nm using a HITACHI 717 (Roche-Hitachi, Indianapolis Ind.).

The OX PERFECT® reagent used for comparison was a commercial reagent sold by Dade Behring Inc., Newark Del. The parameters and recommendations in the package insert for using the reagent were followed.

The adulterants were all prepared as stocks in aqueous medium. PCC is pyridinium chlorochromate. Both methods were calibrated with 2.5 mg/dL of sodium dichromate. The detection limit was defined as the threshold below which the test substance produced an absorbance less than the absorbance of 2.5 mg/dL of solution of sodium dichromate.

Testing was done using the HITACHI 717. The results are summarized in Table 1.

TABLE 1

| Adulterant | Detection Limit (mg/dL) with oX Perfect kit | Detection Limit (mg/dL) with ferric ion |
| --- | --- | --- |
| Iodate | 130 | 60 |
| Iodic acid | 50 | 55 |
| Iodine | 20 | 18 |
| Periodate | 15 | 8 |
| Dichromate | 2.5 | 2.5 |
| Peroxide | 10 | 4 |
| Bleach | 4 | 4 |
| PCC | 5 | 5 |
| Nitrite | 1 | 1 |

The results show that the use of ferric ion enhanced the detection limit of the adulterant. It should be noted that the results for OX PERFECT reagent are the best results obtained from multiple runs and different reagent lots. Accordingly, for some adulterants an enhancement in detection limit was not seen over the commercial reagent at the concentration of ferric ion used.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A test device comprising a support comprising in a dry state an agent for detecting an adulterant in a biological sample and a source of metal ions capable of undergoing reduction by gaining electrons wherein the agent for detecting an adulterant is selected from the group consisting of 2,2-azino-bis(3-ethylbenzthiazoline-6-sulfonic acid, 3-amino-9-ethylcarbazone, naphthols, and phenylamine chromogenic indicators.

2. A test device according to claim 1 wherein the support comprises a strip, plate, well, column, cuvette, test tube, porous member or a support that is part of an automatic device for processing clinical samples.

3. A test device according to claim 1 wherein the metal ions are ferric ions.

* * * * *